United States Patent [19]
Mellul et al.

[11] Patent Number: 5,496,544
[45] Date of Patent: Mar. 5, 1996

[54] POWDERED COSMETIC COMPOSITION CONTAINING A SILICONE FATTY BINDER

[75] Inventors: Myriam Mellul, L'Hay les Roses; Sophie Lecomte, Paris; Isabelle Bara, Paris; Béatrice DeFossez, Paris, all of France

[73] Assignee: L'Oreal, Paris, France

[21] Appl. No.: 140,187

[22] PCT Filed: Mar. 5, 1993

[86] PCT No.: PCT/FR93/00221

§ 371 Date: Jan. 5, 1994

§ 102(e) Date: Jan. 5, 1994

[87] PCT Pub. No.: WO93/17660

PCT Pub. Date: Sep. 16, 1993

[30] Foreign Application Priority Data

Mar. 5, 1992 [FR] France ................................ 92 02654

[51] Int. Cl.$^6$ .......................... A61K 7/02; A61K 7/021; A61K 7/035
[52] U.S. Cl. .......................... 424/78.03; 424/61; 424/63; 424/69; 424/401
[58] Field of Search .................................. 424/78.03, 63, 424/61, 401, 69; 514/951, 952

[56] References Cited

U.S. PATENT DOCUMENTS

| | | |
|---|---|---|
| 4,801,445 | 1/1989 | Fukui et al. .......................... 424/63 X |
| 5,023,075 | 6/1991 | Macchio et al. . |
| 5,061,481 | 10/1991 | Suzuki et al. .......................... 424/63 |
| 5,194,260 | 3/1993 | Grollier et al. ........................ 424/401 |
| 5,385,730 | 1/1995 | Ichinohe .......................... 424/78.03 X |

FOREIGN PATENT DOCUMENTS

| | | |
|---|---|---|
| 0133963 | 1/1986 | European Pat. Off. . |
| 0388582 | 9/1990 | European Pat. Off. . |

OTHER PUBLICATIONS

Patent Abstracts of Japan, vol. 12, No. 198, (C–502) Jun. 8, 1986.
Patent Abstracts of Japan, vol. 11, No. 3 (C–395) Jan. 7, 1987.
Patent Abstracts of Japan, vol. 14, No. 57, (C–684) (4000) Feb. 2, 1990.

*Primary Examiner*—Richard D. Lovering
*Attorney, Agent, or Firm*—Oliff & Berridge

[57] ABSTRACT

A cosmetic composition for skin consisting of an anhydrous powder and mainly including a solid particulate phase mixed with a fatty binder containing a silicone mixture which consists of (a) at least one silicone oil, (b) at least one silicone wax, (c) at least one silicone resin, (d) optionally at least one silicon gum, and (e) optionally at least one phenyldimethicone; wherein components (a), (b), (c), (d) and (e) are present in the binder in concentrations of 12–98.9%, 1–60%, 0.1–25%, 0–3% and 0–20% by weight respectively in relation to the overall weight of the silicone mixture. The composition may be used as face make-up, as eye shadow or as a make-up foundation or powder.

14 Claims, No Drawings

POWDERED COSMETIC COMPOSITION CONTAINING A SILICONE FATTY BINDER

FIELD OF THE INVENTION

The subject of the present invention is a powdered cosmetic composition for the skin, containing a silicone fatty binder.

BACKGROUND

It is known that some cosmetic compositions such as blushers, eye shadows, face powders or foundations, are provided in the form of compacted or cast powders. These are anhydrous compositions called "compact powders", (or "compacts") mainly consisting of a mixture of coloured or non-coloured powders and a fatty binder (oils or mixture of oils and waxes), and shaped by compression, or by casting into a container serving as mould. These powders are generally used by removing a small quantity of powder and then applying to the skin by means of an applicator (sponge, powder puff or brush).

The preparation of binding agents in such compact powders involves many problems. The final product should be sufficiently homogeneous and compact in order to avoid the fragmentation caused especially by impact, while retaining a good disintegration capacity. Moreover, the composition should have a smooth feel and should be easy to spread in a continuous manner. In addition, the binder should be compatible with pigments, and specialists know the problems of degradation of certain pigments when conventional fatty binders are used.

It is known, moreover, that certain make-up compositions are provided in the form of powders called "loose powders", in which the particles are neither compacted nor dispersed in a fatty continuous phase, but retain on the contrary their individuality. Such loose powders often contain a fatty substance (oil) whose role is especially to increase the smoothness of application to promote the adherence of the powder to the skin, and to allow solubilization of some active ingredients. Some loose powders may contain relatively high quantities of oil without the particles having a tendency to agglomerate. Such is the case especially for powders containing particles in the form of hollow microspheres made from synthetic thermoplastic materials see especially Patent EP-0,254,612. But the formulation of such loose powders poses the problem, which is already mentioned above, of the degradation of certain pigments in the presence of the fatty substances conventionally used.

In the present application, the expression "fatty binder" denotes a fatty substance or a mixture of fatty substances constituting the binder for the compacted or cast powders as well as a fatty substance or mixture of fatty substances present in the loose powders especially for increasing the smoothness of application and promoting the adherence to the skin.

The use, as binding agents, in a compacted powder, of silicone oils, which are low-viscosity linear polysiloxanes (polydimethyl siloxane or analogue, abbreviated PDMS), in combination with high-viscosity PDMS compounds (silicone gums), is described in Patent Application JP-61-180707.

The use, as binders, of silicone resins (three-dimensional polycondensation products), in combination with volatile silicones, in cosmetic powders has also been recommended; see for example Patent Applications JP-61-065809, JP-61-161211 and JP-62-298512.

Anhydrous cosmetic compositions containing coated pigments, dispersed in a PDMS-based binder, optionally in combination with a substituted linear polysiloxane (silicone wax), with a cyclic polysiloxane and/or with a conventional wax, have been described in Patent Application EP-133 963. The pigments are coated by chemical bonding with a polysiloxane in order to allow their dispersion in the binder.

A study of these various constituents has shown that low-viscosity silicone oils, mixed with silicone gums, are useful because they confer, especially on the composition, properties of smoothness, ease of spreading and homogeneity. But the make-up behaviour properties and the fallimpact resistance properties of the compact are poor.

Polysiloxane waxes make it possible to obtain a good ease of spreading and an acceptable homogeneity of the make-up and improve the mechanical properties (resistance to fallimpact). But the behaviour properties are not satisfactory.

Silicone resins confer good behaviour and fall-impact resistance properties, but the compositions lack smoothness.

It should be noted that the combination of two classes of silicone binders generally does not bring about notable improvement of the properties.

Accordingly, the addition of a silicone resin to high- and low-viscosity PDMS compounds reduces the ease of spreading, whereas, separately, the two constituents give compositions which are easy to spread. Likewise, the homogeneity individually provided by the two constituents deteriorates when they are combined. On the other hand, the behaviour is improved.

The addition of a low-viscosity silicone oil to a silicone resin does not improve the smoothness and notably reduces the ease of spreading and the homogeneity.

It has now been discovered that the combination of three classes of silicones (oils, waxes and resins), optionally combined with silicone gums, in the preparation of the fatty binder, makes it possible to obtain powders whose cosmetic properties as a whole are improved or maintained at a very satisfactory level. In addition, such a binder is compatible with all the pigments used in cosmetic powders, including easily degradable mineral pigments such as manganese violet or chromium oxides. Furthermore, the binder conforming to the invention does not require the coating of the pigments in order to facilitate their dispersion.

SUMMARY OF THE INVENTION

The subject of the present invention is therefore a cosmetic composition for the skin, in the form of an anhydrous powder mainly comprising a solid particulate phase mixed with a fatty binder containing a silicone mixture, characterized by the fact that the said silicone mixture consists of:

(a) at least one silicone oil, (b) at least one silicone wax, (c) at least one silicone resin, (d) optionally at least one silicone gum, and (e) optionally at least one phenyl dimethicone, and in that the said constituents (a), (b), (c), (d) and (e) are present in the hinder respectively at concentrations of 12–98.9%, 1–60%, 0.1–25%, 0–3% and 0–20% weight relative to the total weight of the silicone mixture.

DESCRIPTION OF PREFERRED EMBODIMENTS

The composition according to the invention may he a loose powder, a compact powder or a cast powder.

Preferably, the concentrations of the constituents of the silicone mixture, by weight relative to the total weight of the said mixture, are the following:

pure silicone gum: 0–0.4%
silicone wax: 2–50%,
pure silicone resin: 0.5–15%,
phenyl dimethicone: 0–15%,
silicone oil: qs 100%.

In a specific embodiment, the fatty binder consists only of a silicone mixture as defined above.

It is known that low-viscosity silicone oils are linear polysiloxanes consisting (except for the terminal groups) of units of formula (I)

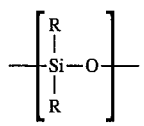     (I)

in which each substituent R independently represents a lower alkyl group (having 1 to 6 C).

The degree of polymerization (number of repeating units) of these low-viscosity polysiloxanes may range for example from about 3 to 2000.

These low-viscosity silicone oils can be prepared according to known methods, or bought commercially: for example series 47 Silbione oil (RHONE POULENC), series 200 oil (DOW CORNING), SF 96 oil (GENERAL ELECTRIC).

The terminal groups are for example trimethylsilyl, dimethyl hydroxymethylsilyl or vinyl dimethylsilyl groups.

The silicone gums which can be used, in conformity with the present invention, are polysiloxanes having high molecular masses which may range for example from 200,000 to 1,000,000. They are used alone or in the form of a mixture in a solvent. This solvent may be chosen especially from polydimethyl siloxane oils (PDMS) and polyphenylmethyl siloxane oils (PPMS). They are also known and commercial products, or products which can be prepared according to known methods. The following silicone gums may be mentioned more particularly: polydimethyl siloxane/methyl vinyl siloxane, polydimethyl siloxane/diphenyl siloxane, polydimethyl siloxane/phenylmethyl siloxane, and polydimethyl siloxane/diphenyl siloxane/methyl vinyl siloxane. Among the commercial silicone gums, there may be mentioned those sold under the name SE30 (GENERAL ELECTRIC), TP232 (UNION CARBIDE), Q2-1403 (DOW CORNING), or the VISCASIL series (GENERAL ELECTRIC).

The silicone waxes which can be used in the fatty binder of the present invention are substituted polysiloxanes which are solid or liquid at room temperature. They are preferably low-melting point fluids or solids. They are especially substituted linear polysiloxanes essentially consisting (apart from the terminal groups) of units of the formulae II and III, in the respective molar proportions m and n:

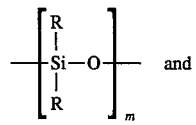     (II)

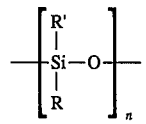     (III)

in which each substituent R is defined as above, each R' independently represents an optionally unsaturated alkyl (linear or branched) having 6–30 carbon atoms, or alternatively a group —X—R", each X independently represents:

—O—,

—(CH$_2$)$_a$—O—CO—,

—(CH$_2$)$_b$—CO—O—, a and b independently represent numbers which may range from 0 to 6, and each R" independently represents an optionally unsaturated alkyl group having 6 to 30 carbon atoms m is a number which may range from 0 to 400, and in particular from 0 to 100, n is a number which may range from 1 to 200, and in particular from 1 to 100, the sum (m+n) being less than 400, and in particular less than or equal to 100.

These silicone waxes are known or may be prepared according to known methods. Among the commercial silicone waxes of this type, there may be mentioned especially those sold under the names Abilwax 9800, 9801 or 9810 (GOLDSCHMIDT), KF910 and KF7002 (SHIN ETSU), or 176-1118- 3 and 176-11481 (GENERAL ELECTRIC).

The silicone waxes which can be used may also be chosen from the compounds of formula IV

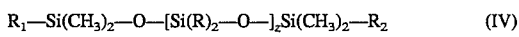     (IV)

in which R is defined as above,

R$_1$ represents an alkyl group of 1 to 30 C, an alkoxy group of 6 to 30 C, or a group of formula:

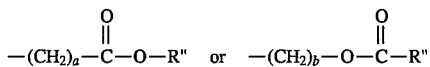

R$_2$ represents an alkyl group of 6 to 30 C, an alkoxy group having from 6 to 30 C or a group of formula:

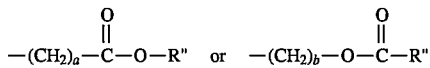

a and b representing a number from 0 to 6,

R" being a C$_6$ to C$_{30}$ alkyl, and z is a number which may range from 1 to 100.

Among the silicone waxes of formula IV, which are known products or which can be prepared according to known methods, there may be mentioned especially the following commercial products: Abilwax 2428, 2434 and 2440 (GOLDSCHMIDT), or VP 1622 and VP 1621 (WACKER).

Silicone resins are hydrolysis and polycondensation products of mixtures of siloxanes of formulae (R)$_3$SiOCH$_3$ and Si(OCH$_3$)$_4$, R representing an alkyl group having from 1 to 6 C.

These silicone resins are known or may be prepared according to known methods. Among the commercial silicone resins which can be used, there may be mentioned for example those which are sold under the names DC 593 (DOW CORNING) or SS4230 (GENERAL ELECTRIC).

Phenyl dimethicones are known products corresponding to the formula VI:

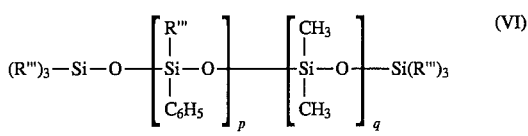

in which q is a number which may range from 0 to 5,000, p is a number which may range from 1 to 5,000, and each R''' independently represents a methyl, phenyl or trimethylsilyloxy group.

These phenyl dimethicones may be used as optional ingredients which make it possible to improve the smoothness of the application.

Generally, the fatty binder may represent from 0.5 to 25% by weight, preferably from 3 to 20%, relative to the total weight of the composition.

The particulate phase of the composition consists of the pigments and/or fillers customarily used in such cosmetic compositions. The pigments are chosen from inorganic and/or organic pigments, and/or pearlescent pigments.

These pigments may represent up to 70% of the weight of the final composition.

Among the inorganic pigments there may be mentioned, by way of example:

titanium dioxide (rutile or octahedrite), optionally superficially treated and codified in the Color Index under the reference CI77891;

black, yellow, red and brown iron oxides, codified under the references CI77499, 77492, 77491;

manganese violet (CI 77742);

ultramarine violet (CI 77007);

ultramarine blue (CI 77007);

chromium oxide (CI 77288);

hydrated chromium oxide (CI 77289) and ferric blue (CI 77510).

Among the organic pigments, there may be mentioned, in particular, the pigments:

D & C red No. 3 (CI 45430:1)

D & C red No. 6 (CI 15850:2)

D & C red No. 7 (CI 15850:1)

D & C red No. 9 (CI 15585:1)

D & C red No. 13 (CI 15630:3)

D & C red No. 19 (CI 45170)

D & C red No. 21 (CI 45380:2)

D & C red No. 27 (CI 45410:1)

D & C red No. 30 (CI 73360)

D & C red No. 36 (CI 12085)

carbon black (CI 77266) and lacquers based on carmine (CI 75470).

The pearlescent pigments may be chosen especially from white pearlescent pigments such as mica coated with titanium oxide or bismuth oxychloride. There may also be used coloured pearlescent pigments such as mica-titanium coloured with iron oxides, mica-titanium coloured with ferric blue or chromium oxide, mica-titanium coloured with an organic pigment of the abovementioned type, as well as pearlescent pigments based on bismuth oxychloride.

The fillers are chosen especially from:

talc, which is a hydrated magnesium silicate, used in the form of particles generally less than 40 μm in size; talc has moisture-absorbing properties and is used especially because of its unctuous feel;

micas, which are aluminosilicates of varied compositions, which exist in the form of scales which are 2 to 200 μm, preferably 5 to 70 μm in size and have a thickness of 0.1 to 5 μm, preferably 0.2 to 3 μm. Micas may be of natural origin (for example muscovite, margarite, roscoelite, lipidolite, biotite) or of synthetic origin. The micas are generally transparent and make it possible to confer a satiny appearance on the skin;

modified or unmodified starch, in particular rice starch;

silica;

alumina;

boron nitride;

kaolin, which is a hydrated aluminium silicate, which exists in the form of particles of isotropic shape, and which has good fat-absorbing properties;

zinc and titanium oxides: these oxides have an unctuous feel, a good covering power and a high opacity; the nanopigment forms of these products can also be used;

precipitated calcium carbonate which, in the form of particles of less than about 10 μm in size, has an unctuous feel and makes it possible to obtain a matt appearance;

magnesium carbonate or hydrocarbonate, which possess especially perfume-binding properties;

metallic soaps derived from a carboxylic organic acid having 8 to 22 carbon atoms, preferably 12 to 18 carbon atoms, for example zinc, magnesium or lithium stearate, zinc laurate, magnesium myristate and the like. These soaps, generally present in the form of particles of less than 10 μm in size, have an unctuous feel and facilitate the adherence of the powder to the skin;

synthetic polymer (or copolymer) powders chosen from polyethylene and its derivatives (for example: polytetrafluoroethylene, polystyrene and the like), polyacrylates, polymethacrylates, polyesters or polyamides and the like, for example nylon powders powders in the form of hollow microspheres made from thermoplastic synthetic material, whose hollow part contains a gas.

The hollow microspheres are prepared according to known processes, such as those described in Patent FR 3,615,972 or European Patent Application No. 0,056,219.

These microspheres can be prepared from any non-toxic and non-irritant thermoplastic material. These materials may be for example polymers or copolymers of ethylene derivatives (for example polyethylene, polystyrene, vinyl chloride-acrylonitrile copolymer and the like) of polyesters, urea-formaldehyde polymers, vinylidene chloride copolymers (for example vinylidene chlorideacrylonitrile), and the like.

The fillers may represent up to 95% of the total weight of the composition of the invention.

The pigments and fillers may be coated, if desired, with substances such as especially amino acids, silicones, metallic soaps or collagen, especially so as to modify the state of their surface. The surface state may also be modified by chemical grafting or adsorption of silicone molecules, other molecules, such as triisostearoyl titanate, also being suitable.

Various customary additives may also be introduced into the composition. Generally, these additives, taken together, do not represent more than 10%, and especially not more than 5% by weight relative to the total weight of the composition. The composition of the invention may therefore contain at least one additive chosen especially from antiseptics (for example trichlorodiphenyl ether, cationic agents, boric acid and the like) which are used especially in deodorant powders for the body or the feet and in baby powders; astringent agents, which are used in deodorant powders or in foot powders, such as aluminium hydroxychloride or alums; sunscreen agents; cicatrizing agents; anti-free radical agents; vitamins, demulsent agents; emollient agents, especially oils such as esters of fatty acids with a $C_{10}$ to $C_{22}$ fatty alcohol or with a lower alcohol (for example triisocetyl citrate, myristyl myristate and the like) or vegetable oils (especially jojoba oil and the like), mineral oils (especially vaseline oil and the like) or oils of animal origin (especially lanolin and the like); moisturizing agents (glycerol, sorbitol and the like); depigmenting agents; perfumes; consistency agents (natural or synthetic gums); and the like.

The compositions of the invention may be provided especially in the form of blushers, eye shadows, face make-up powders, body powders (perfumed and/or deodorizing), including foot powders and the like.

The compositions of the invention can be prepared according to the usual methods, for example according to one of the following processes:

Process 1: (for compacted powders)

In a first stage, the pigments and/or fillers, as well as the powdery additives are mixed, then the binder and/or optionally the consistency agents as well as other optional ingredients are added, and the whole is mixed and/or optionally ground.

The binder may be optionally heated if necessary.

The mixture is then compacted by means of a press in metal cups.

Process 2: (for cast powders)

All the constituents of the formula are mixed and suspended in a solvent (water, hexane, isopropanol, ethanol and the like).

The paste obtained is then cast into a cup, then the solvent is evaporated.

Process 3: (for loose powders)

The pigments and/or fillers as well as the powdery additives are mixed, then the binder and, optionally, the consistency agents as well as other optional ingredients are added and the whole is mixed and optionally ground.

Where appropriate, the binder is heated. If desired, the mixture may be sifted before packaging in a suitable container.

The subject of the invention is also the use of a silicone mixture as binding agent, in the preparation of an anhydrous cosmetic composition provided in the form of a powder (loose, compacted or cast) mainly consisting of solid particles mixed with a fatty binder, the said silicone mixture being as defined above. The compositions obtained are applied to the skin according to the usual methods.

The following examples illustrate the invention. In these examples, the quantities of the various ingredients are given in parts by weight.

EXAMPLE 1

Blusher

| Part A | |
|---|---|
| Titanium dioxide | 10.00 |
| Mica-titanium | 10.00 |
| Zinc stearate | 4.00 |
| D & C Red 30 | 0.50 |
| Talc | 69.30 |

| Part B | |
|---|---|
| Cetyl dimethicone | 0.08 |
| Behenoxy dimethicone | 1.60 |
| Trimethylsiloxysilicate at 33% in a low-viscosity PDMS | 0.53 |
| High-viscosity polydimethyl siloxane containing 14% active material in a low-viscosity PDMS | 0.01 |
| Low-viscosity polydimethyl siloxane | 3.78 |
| Preservatives | 0.2 |
| | 100.00 |

Origin of the products: Cetyl dimethicone: Abilwax 9801 (GOLDSCHMIDT) Behenoxy dimethicone: Abilwax 2440 (GOLDSCHMIDT) Trimethylsiloxysilicate at 33% in a low-viscosity PDMS;

DC593 (DOW CORNING)

High-viscosity polydimethyl siloxane : Q2-1403 (DOW CORNING) : 14% solution in a low-viscosity PDMS. Low-viscosity polydimethyl siloxane : PDMS 10 centi-stockes, marketed by the company GOLDSCHMIDT.

Procedure:

1) Mix the constituents of phase A.

2) Add phase B. Mix again.

3) Grind if necessary.

4) Sift.

5) Compact in a metal cup.

This formula is very easy to disintegrate and gives a very homogeneous make-up.

EXAMPLE 2

Compacted face powder

| Part A | |
|---|---|
| Sericite | 65.80 |
| Mica | 15.00 |
| Polyethylene powder | 5.00 |
| Titanium dioxide | 2.00 |
| Iron oxides | 8.00 |

| Part B | |
|---|---|
| Cetyl dimethicone | 0.15 |
| Behenoxy dimethicone | 0.30 |
| Trimethylsiloxysilicate (DC 593) | 0.75 |
| Low-viscosity polydimethyl siloxane | 2.80 |
| Preservatives | 0.2 |
| | 100.00 |

Origin of the products: see Example 1

Procedure: that of Example 1

This product exhibits great smoothness on application.

EXAMPLE 3

Eye shadow

| Part A | |
|---|---|
| Mica-titanium | 40.00 |
| Green chromium oxide | 6.00 |
| Talc | 43.80 |

| Part B | |
|---|---|
| Cetyl dimethicone | 1.24 |

-continued

| | |
|---|---|
| Trimethylsiloxysilicate (DC 593) | 1.98 |
| Low-viscosity polydimethyl siloxane | 6.78 |
| Preservative | 0.20 |
| | 100.00 |
| C. Ethanol | 85.00 |

C. Ethanol

Origin of products: see Example 1

Procedure:

1) Mix the constituents of phase A.
2) Add phase B and phase C and mix again.
3) The paste obtained is cast or injected directly into a cup.
4) The solvent is evaporated.

This product is easy to apply and has great smoothness.

EXAMPLE 4

Eye shadow

| Part A | |
|---|---|
| Mica | 15.00 |
| Polyamide powder | 10.00 |
| Iron oxide | 10.00 |
| Manganese violet | 20.00 |
| Talc | 38.80 |
| Part B | |
| Cetyl dimethicone | 0.21 |
| Behenoxy dimethicone | 0.44 |
| Trimethylsiloxysilicate (DC 593) | 1.12 |
| Low-viscosity polydimethyl siloxane | 4.23 |
| Preservatives | 0.20 |
| | 100.00 |

Origin of products: see Example 1

Procedure:

1) Mix the constituents of phase A.
2) Add phase B and mix again
3) Grind if necessary
4) Sift
5) Compact in a metal cup.

This product is very smooth and very easy to spread.

EXAMPLE 5

Loose powder

| Part A | |
|---|---|
| Mica | 67.50 |
| Polyamide powder | 25.00 |
| Zinc stearate | 2.00 |
| Iron oxides | 1.00 |
| Perfume (impregnated in magnesium carbonate) | 1.5 |

-continued

| | |
|---|---|
| Part B | |
| Abilwax 9801 | 1.5 |
| DC 593 | 0.5 |
| Low-viscosity PDMS | 1.0 |
| | 100.00 |

The low-viscosity PDMS is that marketed under the name Abil 10 (GOLDSCHMIDT).

Procedure:

1) Mix the constituents of part A
2) Add part B and mix again
3) Grind and sift.

Comparative Examples

The properties of compacted powders obtained using, as binding agents, various silicones or silicone mixtures, were studied. In all cases, the particulate phase was the same as in Example 4(A) above, the proportion of binding agent being 6%. The compositions were prepared as in Example 4.

The compositions obtained were tested by users who were to indicate, for the property studied, if the composition tested gave an average result (0), a good result (+) or a very good result (++).

The properties studied were the following:

a) Mechanical properties of the compact fallimpact resistance: the test consists in evaluating the cohesion of the compacted product by measuring the loss of powder mass after 10 standardized fallimpacts from a height of 20 cm, b) Cosmetic properties:

smoothness of application: the test consists in evaluating (sensory evaluation) the smoothness on application;

ease of spreading: the test consists in evaluating the ease of spreading the powder and of depositing it over the entire surface to which make-up is to be applied;

adherence: the test consists in evaluating the capacity of the powder to become deposited and to remain in place on the skin;

behaviour: the test consists in evaluating the capacity of the powder to remain on the skin after 4 hours;

homogeneity: the test consists in evaluating the uniformity of the powder layer on the skin after make-up application.

The compositions studied end the results are summarized in Tables 1 and 2. The compositions studied in Table 2 are compositions according to the invention, whereas the compositions of Table 1 are compositions for comparison.

TABLE 1

Compositions for comparison

| | COMPOSITIONS | | | | | | | | |
|---|---|---|---|---|---|---|---|---|---|
| | 1 | 2 | 3 | 4 | 5 | 6 | 7 | 8 | 9 |
| LOW-VISCOSITY PDMS | 100% | | | | | 60% | 30% | 50% | 50% |
| HIGH-VISCOSITY PDMS* | | 100% | | | | 40% | 20% | | |
| BEHENOXY DIMETHICONE | | | 100% | | | | | | 50% |
| CETYL DIMETHICONE | | | | 100% | | | | 50% | |
| TRIMETHYLSILOXYSILICATE | | | | | 100% | | 50% | | 50% |
| PROPERTIES | | | | | | | | | |
| Fallimpact resistance | 0 | 0 | ++ | + | ++ | 0 | 0 | ++ | + |
| Smoothness on application | ++ | 0 | + | + | 0 | + | + | ++ | 0 |
| Ease of spreading | ++ | + | ++ | + | + | + | + | + | 0 |
| Behaviour | + | 0 | 0 | 0 | ++ | 0 | ++ | 0 | ++ |
| Homogeneity | ++ | + | + | ++ | + | ++ | 0 | ++ | 0 |
| Adherence | 0 | ++ | + | + | + | + | ++ | 0 | + |

Origin of the products: see Example 1
*14% solution of active material dissolved in a low-viscosity PDMS

TABLE 2

Compositions No. 10 to 15 according to the invention

| | COMPOSITIONS | | | | | |
|---|---|---|---|---|---|---|
| | 10 | 11 | 12 | 13 | 14 | 15 |
| CETYL DIMETHICONE | 3.8 | 1.3 | 12.4 | 20.0 | 20.8 | 2.0 |
| BEHENOXY DIMETHICONE | 7.3 | 26.7 | — | 20.0 | 0.5 | 25.0 |
| TRIMETHYLSILOXYSILICATE* | 18.7 | 8.8 | 19.8 | 6.6 | 24.7 | 3.0 |
| HIGH-VISCOSITY PDMS** | — | 0.2 | — | 0.1 | — | 1.0 |
| LOW-VISCOSITY PDMS | 70.2 | 63.0 | 67.8 | 53.3 | 54.0 | 69.0 |
| PROPERTIES | | | | | | |
| Fallimpact resistance | + | + | + | ++ | ++ | + |
| Smoothness on application | ++ | ++ | ++ | + | + | ++ |
| Ease of spreading | + | + | ++ | ++ | + | ++ |
| Behaviour | + | + | ++ | + | ++ | + |
| Homogeneity | + | ++ | ++ | + | ++ | ++ |
| Adherence | ++ | + | + | ++ | + | + |

*containing 33% active material in a low-viscosity PDMS
**containing 14% active material in a low-viscosity PDMS
Origin of the products: see Example 1

2) Results of preservation:

The preceding compositions Nos. 10, 11 and 12 were compared with a composition containing a conventional binder and the same particulate phase. The compositions are preserved in an oven (40° C.) for 2 months.

At the end of this time, the intensity of the odour, scored in the following manner, is evaluated subjectively:

very intense: +++ intense: ++ fairly intense: + no odour: 0

The conventional compositions contained the following binder:

COMPOSITION 16:

vaseline oil: 55% oleyl alcohol: 30% liquid lanolin: 10% castor oil: 5%

COMPOSITION 17 :

vaseline oil: 85% white vaseline: 15%

The results are summarized in Table 3 below:

TABLE 3

| COMPOSITIONS | 10 | 11 | 12 | 16 | 17 |
|---|---|---|---|---|---|
| Odour | 0 | 0 | 0 | +++ | + |

3) Preparation of compositions containing pigments which are difficult to use

It is known that some pigments, such as chromium oxide, ultramarine blue, manganese violet, give formulations which are difficult to use and which are not very homogeneous on make-up application.

The compositions tested were the following:

talc: 40% chromium oxides: 15% mica-titanium coated with chromium oxide: 15% binder: 10%

The chromium oxide used is a 50/50 mixture of chromium oxide and chromium hydroxide.

For the compositions 18, 19 and 20 which were studied, the binding agent was the following:

Composition 18: binder for composition 16

Composition 19: binder for composition 11 (according to the invention)

Composition 20: binder for composition 12 (according to the invention)

The results are summarized in the following table (Table 4):

TABLE 4

| COMPOSITIONS TESTED | 18 | 19 | 20 |
|---|---|---|---|
| Smoothness | 0 | + | + |
| Ease of spreading | + | ++ | ++ |
| Homogeneity | 0 | + | ++ |

What is claimed is:

1. Cosmetic composition for the skin, in the form of an anhydrous powder mainly comprising a solid particulate phase mixed with a fatty binder containing a silicone mixture, characterized by the fact that said silicone mixture consists of:

(a) at least one silicone oil, (b) at least one silicone wax, (c) at least one silicone resin, (d) optionally at least one silicone gum, and (e) optionally at least one phenyl dimethicone, and in that the said constituents (a), (b), (c), (d) and (e) are present in the binder respectively at concentrations of 12–98.9%, 1–60%, 0.1–25%, 0–3% and 0–20% by weight relative to the total weight of the silicone mixture.

2. Composition according to claim 1, characterized by the fact that the concentrations of the constituents of the silicone mixture, by weight relative to the total weight of said mixture, are the following:

silicone wax: 2–50%, silicone resin: 0.5–15%, silicone gum: 0–0.4% phenyl dimethicone: 0–15%, silicone oil: qs 100%.

3. Composition according to claim 1, characterized by the fact that said fatty binder consists of the said silicone mixture.

4. Composition according to claim 1, characterized by the fact that the low-viscosity silicone oil is at least one linear polysiloxane consisting (except for the terminal groups) of units of formula I

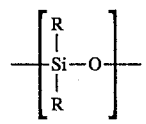

in which each substituent R independently represents a lower alkyl group having 1 to 6 C, said polysiloxane having a degree of polymerization of 3 to 2000.

5. Composition according to claim 1, characterized by the fact that the silicone wax essentially consists of at least one substituted linear polysiloxane essentially consisting (apart from the terminal groups) of units of the formulae (II) and (III), in the respective molar proportions m and n:

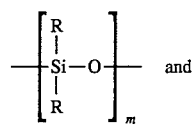

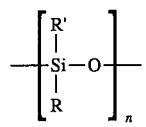

in which each substituent R is an alkyl group having 1 to 6 C, each R' independently represents an optionally unsaturated alkyl having 6–30 carbon atoms, or alternatively a group —X—R", each X independently represents:

—O—,

—(CH$_2$)$_a$—O—CO—,

—(CH$_2$)$_b$—CO—O—, a and b independently represent numbers which may range from 0 to 6, and each R" independently represents an optionally unsaturated alkyl group having 6 to 30 carbon atoms m is a number which may range from 0 to 400, and in particular from 0 to 100, n is a number which may range from 1 to 200, and in particular from 1 to 100, the sum (m+n) being less than 400, and in particular less than or equal to 100.

6. Composition according to claim 1, characterized by the fact that said silicone wax contains at least one compound of the formula IV $$R_1—Si(CH_3)_2—O—[Si(R)_2—O—]_zSi(CH_3)_2—R_2 \qquad (IV)$$

in which each R is an alkyl group having 1 to 6 C, $R_1$ represents an alkyl group having 1 to 30 C, an alkoxy group having 6 to 30 C, or a group:

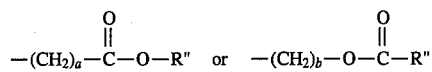

$R_2$ represents an alkyl group of 6 to 30 C, an alkoxy group having from 6 to 30 C or a group:

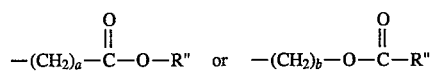

a and b representing a number from 0 to 6, R" being a $C_6$ to $C_{30}$ alkyl, and z is a number which may range from 1 to 100.

7. Composition according to claim 1, characterized by the fact that the said silicone resin consists of hydrolysis and polycondensation products of mixtures of siloxanes of formula (R)$_3$SiOCH$_3$ and Si(OCH$_3$)$_4$, R representing an alkyl group having from 1 to 6 C.

8. Composition according to claim 1, characterized by the fact that said silicone gum is a polysiloxane having a molecular mass of 200,000 to 1 million.

9. Composition according to claim 1, characterized by the fact that said phenyl dimethicone corresponds to the formula VI:

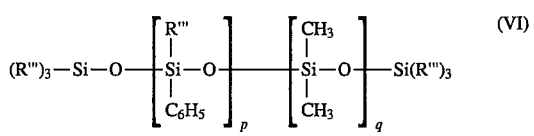

(VI)

in which q is a number which may range from 0 to 5,000, p is a number which may range from 1 to 5,000, and each R''' independently represents a methyl, phenyl or trimethylsilyloxy group.

10. Composition according to claim 1, characterized by the fact that the said silicone mixture represents from 3 to 20% by weight relative to the total weight of the composition.

11. Composition according to claim 1, characterized by the fact that said composition comprises, in addition, at least one additive agent chosen from antiseptics, astringent agents, sunscreen agents, cicatrizing agents, anti-free radical agents, vitamins, demulsent agents, emollient agents, depigmenting agents, perfumes and consistency agents.

12. Composition according claim 11, characterized by the fact that the additives, taken as a whole, do not represent more than 10%, and in particular not more than 5%, of the total weight of the composition.

13. Composition according to claim 1, characterized by the fact that it is provided in the form of an eye shadow, a blusher, a face make-up powder or a body powder.

14. A method for cosmetically treating skin comprising applying to said skin a cosmetic composition containing solid particles and a fatty acid binder, said fatty acid binder comprising a silicon mixture consisting of:

(a) at least one silicone oil, (b) at least one silicone wax, (c) at least one silicone resin, (d) optionally at least silicone gum, and (e) optionally at least one phenyl dimethicone, the said constituents (a), (b), (c), (d) and (e) being present in the binder respectively at concentrations of 12–98.9%, 1–60%, 0.1–25%, 0–3% and 0–20% of the total weight of said silicone mixture.

* * * * *